United States Patent [19]
Bloebaum et al.

[11] Patent Number: 4,883,488
[45] Date of Patent: Nov. 28, 1989

[54] TIBIAL COMPONENT FOR A KNEE PROSTHESIS

[75] Inventors: Roy D. Bloebaum, Salt Lake City, Utah; Frank P. Magee, Phoenix; Thomas P. Murray, Scottsdale, both of Ariz.

[73] Assignee: Harrington Arthritis Research Center, Phoenix, Ariz.

[21] Appl. No.: 206,045

[22] Filed: Jun. 13, 1988

[51] Int. Cl.$^4$ .............................................. A61F 2/38
[52] U.S. Cl. ......................................... 62.3/20; 623/18
[58] Field of Search .................... 603/16, 18, 19, 20, 603/21, 22, 23

[56] References Cited

U.S. PATENT DOCUMENTS

| | | | |
|---|---|---|---|
| 3,488,779 | 1/1970 | Christesen | 623/16 |
| 3,605,123 | 9/1971 | Hahn | 623/16 |
| 4,714,473 | 12/1987 | Bloebaum | 623/20 |
| 4,759,767 | 7/1988 | Lacey | 623/20 |

Primary Examiner—Richard J. Apley
Assistant Examiner—David J. Isabella
Attorney, Agent, or Firm—Kelly, Bauersfeld & Lowry

[57] ABSTRACT

An improved tibial component is provided for a knee prosthesis, wherein the tibial component includes a pair of tibial tray members adapted to accommodate independent longitudinal shifting during patient function while retaining a secure and stable fixation with respect to patient bone. The two tibial tray members comprise medial and lateral members for supporting the medial and lateral condyles of a knee joint. These tray members are interconnected by a slide key arrangement which restrains the tibial tray members against relative movement in the anterior-posterior and medial-lateral directions, while permitting relative shifting in a longitudinal direction corresponding generally with a central axis of the patient's tibia. In the preferred form, the two tibial tray members cooperatively define a common anchoring post and include one or more antirotation fins for mechanically locking with patient bone. In addition, in the preferred form, the two tray members include appropriate bone ingrowth surfaces for secure noncemented attachment to patient bone.

14 Claims, 3 Drawing Sheets

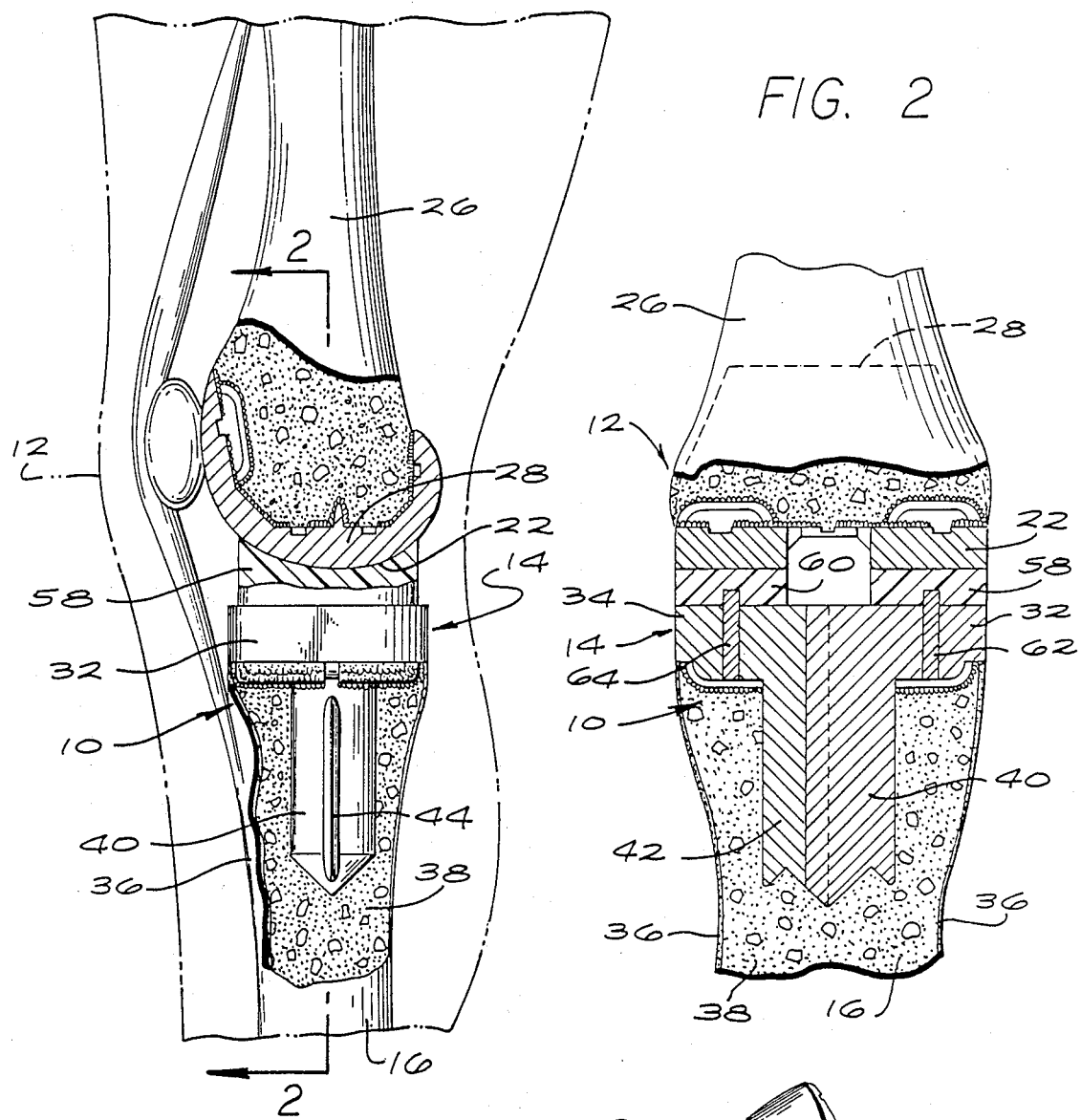
FIG. 2
FIG. 1
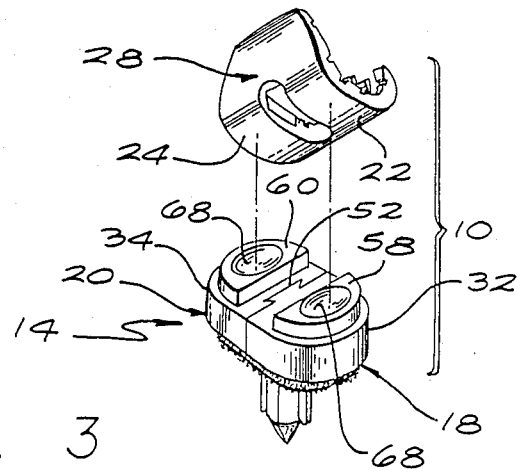
FIG. 3

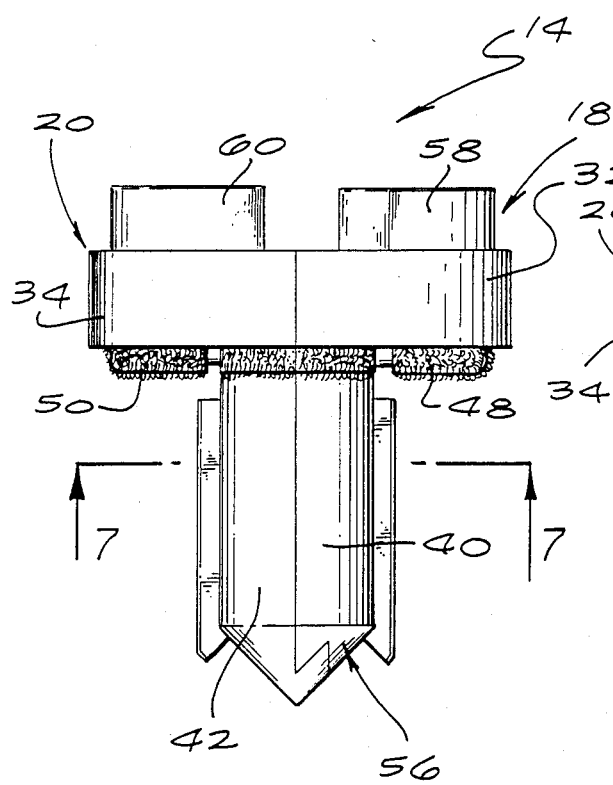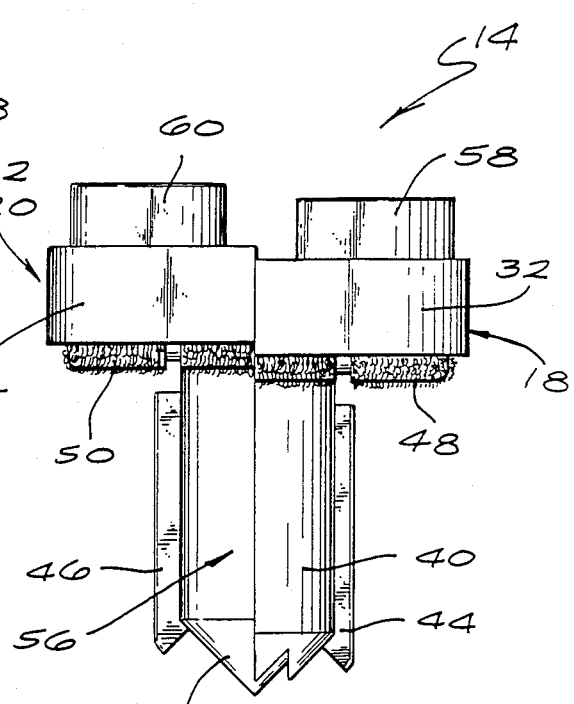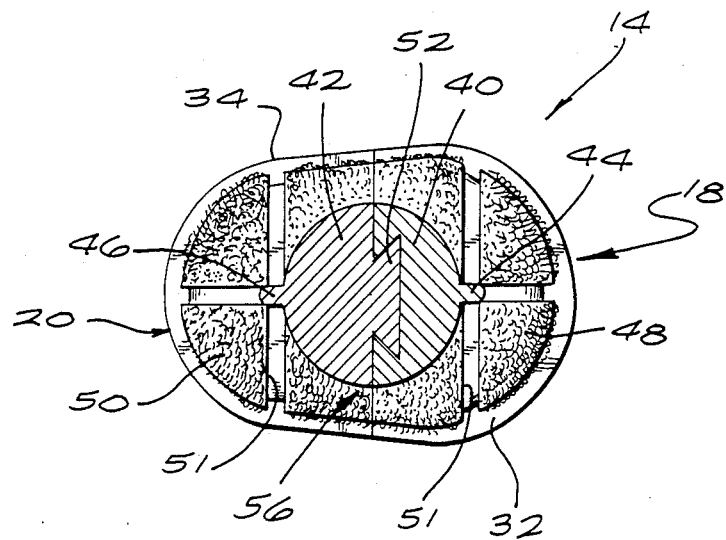

TIBIAL COMPONENT FOR A KNEE PROSTHESIS

BACKGROUND OF THE INVENTION

This invention relates generally to improvements in prosthetic devices used for reconstruction of the knee joint in humans. More particularly, this invention relates to an improved tibial component for use in a knee prosthesis, wherein the tibial component provides improved load bearing capability during normal postoperative patient function.

Artificial or prosthetic joint mechanisms for implantation into animals, particularly humans, have been the subject of intensive research and development efforts for many years. Such prosthetic joint mechanisms have typically comprised one or more implant components formed from a relatively biostable material having selected structural properties and a unique shape to replace all or part of a selected anatomical joint, for example, a hip or knee joint. The implant components are installed by surgically accessing the joint and by resection of one or more bone surfaces to accommodate direct attachment thereto of the implant components. In the past, attachment of implant components to patient bone has been commonly achieved by use of bone cements, such as a methyl methacrylate based cement or the like used as a grouting material to fill up the space between the receptive bone surface and the prosthetic component. More recently, however, a variety of structural and biological incompatibility problems encountered with the use of bone cements have led to the development of so-called bone ingrowth materials. In such bone ingrowth materials, a surface coating of controlled porosity is provided on a prosthesis component in a position for intimately contacting patient bone to achieve a significant degree of postoperative bone and/or tissue ingrowth, and thereby obtain a mechanical interlock with patient bone without utilizing bone cement.

The human knee joint has presented particularly difficult problems in the development of a satisfactory prosthetic joint. More specifically, the human knee joint is recognized as an extremely complex mechanical structure which is subjected to high mechanical loads of widely varying magnitude and direction during normal function. Unfortunately, the knee joint is also subject to a relatively high frequency of disabling injury occurrence. As a result, a wide variety of knee prostheses have been proposed in the prior art, typically to include matingly configured femoral and tibial components adapted respectively for implantation onto the lower end of a resected femur and the upper end of a resected tibia, with appropriate plastic meniscal bearing components interposed therebetween. In the majority of these prior art knee prostheses, the general configuration of the femoral and tibial components has resembled the general physiology of the natural knee joint, namely, to include medial and lateral condyles on the femoral component which are supported by the meniscal bearing components on the tibial component.

However, notwithstanding the many knee prosthesis designs which are available in the art, prior knee prostheses have exhibited an unacceptably limited mechanical load bearing capacity and/or have been subjected to an unacceptably high risk of premature failure. Such failure of the prosthesis most commonly occurs by loosening or detachment of the load bearing tibial component relative to the patient's tibia. When this occurs, surgical revision of the reconstructed knee joint is necessary if the patient is to remain of regain any significant level of ambulation. Unfortunately, surgical revision entails undesirable patient trauma, risk of infection, and general disruption and deterioration of the vascular system in the region of the reconstructed knee. Moreover, in many patients, loss or deterioration of bone structure at the knee joint can make revision surgery extremely difficult and frequently impossible. As a result, knee prostheses have been utilized to date on an extremely limited basis.

One of the major problems encountered with knee prostheses is the inability to insure stable and secure fixation of the tibial component onto the upper end of the patient's tibia. More particularly, secure fixation of the tibial component in a permanent manner is crucial to obtaining satisfactory prosthesis performance, since it is the tibial component which must withstand the high and variant mechanical loads typically of a compressive nature, during normal patient movements. In this regard, during implantation surgery, the upper end of the patient's tibia is resected to expose the asymmetric cross section of the tibia defined by a hard outer shell of cortical bone surrounding a softer interior filled with porous cancellous bone. Ideally, a tibial component is selected to have size and shape to rest securely upon the cortical shell without significant overlap outside the cortical margin in any direction. However, it is frequently difficult for surgeon to insure precision placement of the tibial component in a position fully supported by the hard cortical bone. If any portion of the implant periphery is supported by the softer cancellous bone, the implant can experience tipping or subsidence when subjected postoperatively to normal patient loading, with the result that the implant will work loose over a period of time. Moreover, inherent uneven mechanical loading of the tibial component, particularly in the medial-lateral plane, can also cause the implant to tip and work loose over a period of time.

There exists, therefore, a significant need for an improved tibial component for a knee prosthesis, wherein the tibial component is designed to withstand normal bearing loads during normal patient function without working loose relative to patient bone, and particularly wherein the tibial component is designed to accommodate the inherent uneven loading without risking the necessary secure and stable attachment to patient bone. The present invention fulfills these needs and provides further related advantages.

SUMMARY OF THE INVENTION

In accordance with the invention, an improved tibial component for a knee prosthesis includes a pair of individual tibial tray members for separately supporting the medial and lateral femoral condyles in a reconstructed knee. The two tibial tray members are interconnected by a slide key arrangement or the like to permit limited displacement therebetween along a primary axis of compression loading during use, while maintaining secure and stable individual fixations to patient bone.

In the preferred form of the invention, the improved tibial component for a knee prosthesis comprises medial and lateral tibial tray members each adapted to carry a meniscal bearing component for respectively engaging and supporting the associated femoral condyle of a natural or reconstructed femur. The medial and lateral tibial tray members separately include elongated anchor stems for secure seating into the upper end of a resected tibia, together with at least one antirotation fin to prevent rotation of the prosthesis member relative to a longitudinal axis of the patient's tibia. Importantly, the two tibial tray members are interconnected by the slide key arrangement designed to constrain the tibial tray members against relative displacement in the anterior-posterior plane or the medial-lateral plane, while permitting relative displacement in the direction of the longitudinal tibial axis. Accordingly, after implantation, the tibial tray members may undergo minor longitudinal displacement relative to each other while retaining individual stable fixation to patient bone. In the preferred form, such fixation is obtained in part by use of appropriate porous bone ingrowth surfaces at selected exterior regions on the tibial tray members.

The preferred means for interconnecting the two tibial tray members comprises the slide key arrangement which joins the anchoring stems of the two members into a single anchoring post for the tibial component. More particularly, the anchoring stems for the medial and lateral tray components respectively include a longitudinally elongated slide key of dovetail configuration or the like for mating nd longitudinal slide-fit reception into a similarly elongated key track. The slide key and key track are shaped to lock the two tibial tray components against relative displacement in the anterior-posterior and medial-lateral directions. However, the slide key and key track effectively permit displacement between the two tray members along a longitudinal axis of interconnection between the anchoring stems, wherein this longitudinal axis corresponds with the primary axis of compression loading during use of the prosthesis.

The interlocked tibial tray members are implanted together as an assembled unit, with appropriately sized meniscal bearing components for condylar engagement with minimum or controlled laxity in the reconstructed knee joint. The assembled tibial component provides a stable platform supporting the medial and lateral condylar loads applied thereto during normal patient function. However, in the event of tibial bone subsidence for any reason, the slide key and key track permit longitudinally constrained shifting of the tray members without incurring twisting or torque loads which could otherwise cause the entire tibial component to work loose and fail.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a lateral or outboard side elevation view, partially in vertical section, illustrating a knee prosthesis including a tibial component embodying the novel features of the invention and shown implanted into the knee of a patient;

FIG. 2 is a medial-lateral vertical sectional view taken generally on the line 2—2 of FIG. 1;

FIG. 3 is an exploded perspective view illustrating the tibial component embodying the invention in combination with an exemplary femoral component to provide a total knee prosthesis;

FIG. 5 is a front elevation view of the assembled tibial component;

FIG. 6 is a front elevation view similar to FIG. 5, but depicting accommodation of longitudinal shifting between the tibial tray members; and FIG. 7 is a horizontal sectional view taken generally on the line 7—7 of FIG. 6.

DETAILED DESCRIPTION OF THE PREFERRED EMBODIMENT

Figure 4:
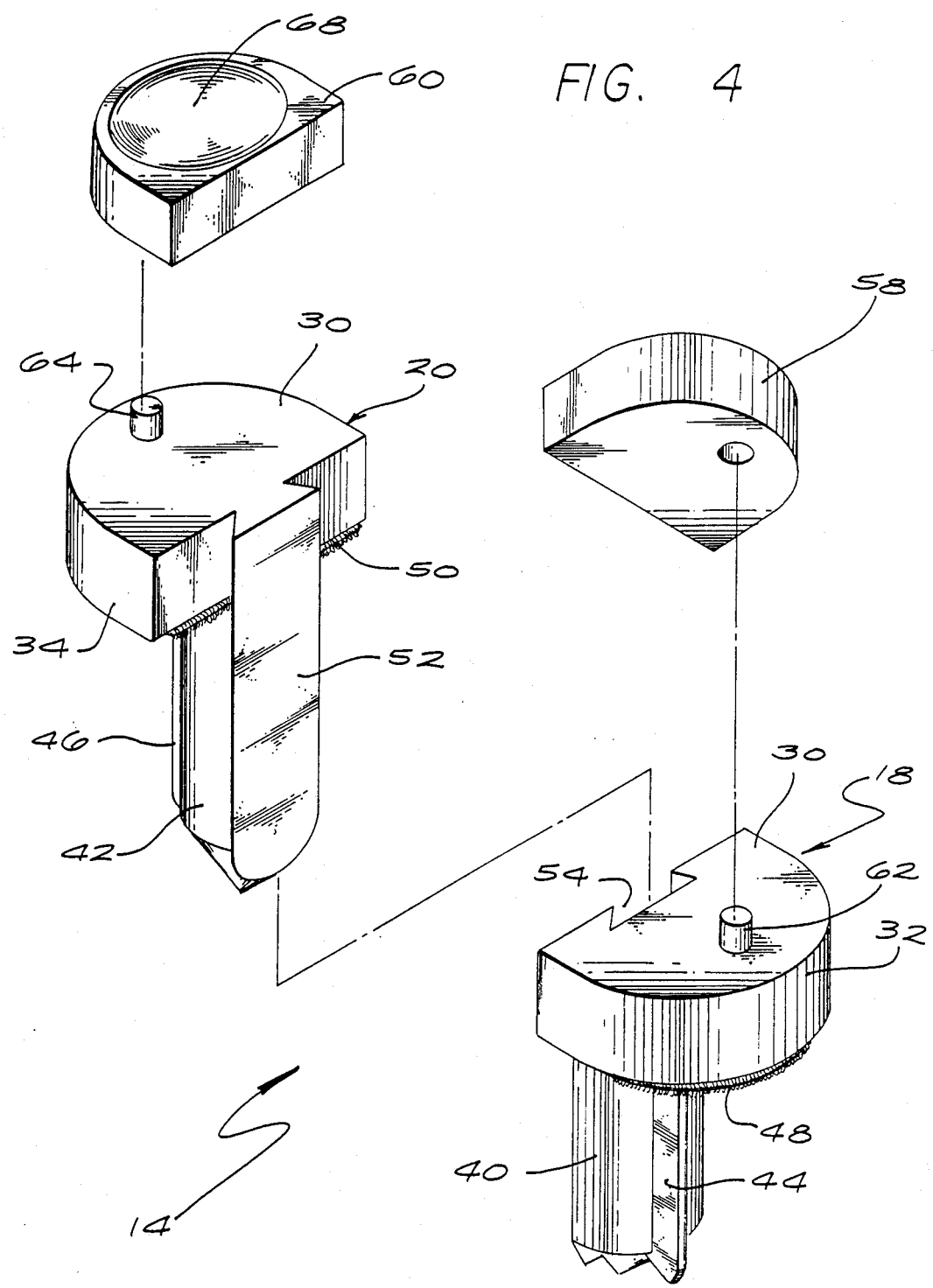
FIG. 4 is an enlarged exploded perspective view showing assembly of a pair of tibial tray members forming the tibial component.

As shown in the exemplary drawings, a knee prosthesis referred to generally by the reference numeral 10 is provided for implantation into the knee 12 of a patient, as viewed in FIG. 1. In accordance with the invention, the knee prosthesis includes an improved tibial component 14 adapted for secure and stable fixation onto the upper end of a patient's resected tibia 16 as a prosthetic replacement for the natural bone surfaces, wherein the improved tibial component 14 is designed to accommodate at least some positional shifting during normal patient function without sacrificing secure and stable fixation to patient bone.

The improved tibial component 14 of the present invention generally comprises a pair of separable or individual tibial tray members 18 and 20 (FIGS. 2-7) for separately supporting mechanical loads at the medial and lateral sides of the knee joint, respectively, during normal patient movements. Accordingly, the two tibial tray members 18 and 20 are adapted to provide individual support for the medial and lateral condyles 22 and 24, respectively, at the lower end of a patient's femur 26. Importantly, since the mechanical loads supported by the tray members 18 and 20 are inherently nonuniform, and further in view of frequent asymmetric loading capacity provided by a resected tibia 16, the two tibial tray members 18 and 20 are designed to accommodate axial or longitudinal shifting therebetween to permit both tray members to remain in a securely fixated relation on the tibia 16 at all times. However, as will be described in more detail, the tibial tray members 18 and 20 are interlocked against relative shifting movement in the anterior-posterior and medial-lateral directions. This permission of longitudinal tray member shifting restricted to a single axis, which corresponds generally with a central axis of the tibia and a primary axis of tibial component compression loading during use of the prosthesis, permits the tibial component to remain in secure and stable attachment to the tibia 16 throughout a normal service life.

As shown generally in FIGS. 1 and 2, the improved tibial component 14 is designed for implantation into the knee 12 as a prosthetic reconstruction for the natural bone structure at the upper and of the tibia 16. In accordance with conventional knee prosthesis implantation procedures, the tibial component 14 is implanted by surgically accessing the patient's knee joint 12 and by resecting the upper end of the tibia 16 to an appropriate geometry for receiving and supporting the tibial component in a secure and stable manner. At the same time, the lower end of the patient's femur 26 is normally resected to an appropriate geometry for implantation of an associated femoral component 28 having the medial and lateral condyles 22 and 24 formed thereon. While the specific construction and implantation method may vary with respect to the femoral component 28, one preferred femoral component is shown and described in U.S. Pat. No. 4,714,473, which is incorporated by reference herein. Alternately, in some cases, reconstruction of the femur 26 may not be required, in which case the lower end of the femur 26 will remain intact with its natural medial and lateral condyles for respectively engaging the tibial tray members 18 and 20, as will be described.

The tibial component 14 is formed by assembly of the two tibial tray members 18 and 20. When these tray members are assembled, as viewed in FIGS. 1-3 and 5-7, the tibial component has a generally conventional overall shape defining a stable, anchored bearing platform 30 at the upper end of the resected tibia 16. This bearing platform 30 has an overall, generally oval but somewhat asymmetric shape adapted to overlie the resected tibia 16 in a mating manner without significant extension beyond the periphery of the tibia. More particularly, the bearing platform 30 is defined by an upper platform member 32 on the medial tray member 18 in cooperation with a slightly smaller upper platform member 34 on the lateral tray member 20. Together, these platform members 32 and 34 are sized to overlie the hard outer shell of cortical bone 36 (FIGS. 1 and 2) of the tibia 16, wherein this cortical bone 36 encases softer, internal cancellous bone 38.

The two tibial tray members 18 and 20 each further include individual anchoring stems and antirotation fins for secure mechanical interlock with the tibia 16. More specifically, the medial tray member 18 includes an anchoring stem 40 projecting downwardly from the underside of the medial platform member 32. Similarly, the lateral tray member 20 has an anchoring stem 42 which projects downwardly from the underside of the lateral platform member 34. These anchoring stems 40 and 42, in the preferred form of the invention, respectively carry an associated pair of elongated and outwardly projecting antirotation fins 44 and 46. The anchoring stems and the antirotation fins are designed to project downwardly into the cancellous bone 38 at the upper end of the tibia 16 for securely locking the two tray members 18 and 20 in place.

Enhanced fixation of the tibial tray members 18 and 20 is achieved by use of porous ingrowth material surface coatings 48 and 50 on selected surfaces thereof, such as on the underside of both platform members 32 and 34. These surface coatings are formed and constructed in a manner known to those skilled in the art, and may beneficially be combined with bulged and/or contoured surfaces in combination with fluid drainage channels 51 as referenced, for example, in U.S. Pat. No. 4,714,473. Such surface coatings function postoperatively to accommodate ingrowth of patient bone and/or tissue to achieve a secure mechanical interlock between the prosthesis and the bone without requiring use of a bone cement.

In accordance with a primary aspect of the invention, the two tibial tray members 18 and 20 are interconnected in a manner permitting selected relative movement therebetween when implanted into the knee joint. In general terms, the interlock between the tibial tray members comprises a slide key interconnection or the like which restricts relative movement between the tray members to a single axis or direction. Importantly, this axis of permitted motion corresponds generally with the longitudinal axis of the patient's tibia 16, and thus also corresponds with the primary direction of compression loading of the tibial component 14 during normal patient function.

As shown best in FIGS. 3, 4 and 7, the preferred slide key interconnection between the tibial tray members 18 and 20 comprises a longitudinally elongated, generally upright slide key 52 of dovetail cross section or the like formed at the medially inboard side of the lateral tray member 20. This slide key 52 is formed as an integral part of the platform member 34 and the underlying stem 42. The slide key 52 is sized and shaped for mating slide-fit reception into a conformingly shaped key track 54 formed in the laterally outboard side of the medial tray member 18, wherein this key track 54 also extends longitudinally as an integrated portion of the platform member 32 and underlying stem 40. When the slide key 52 is received into the key track 54, the two platform members 32 and 34 cooperatively define the tibial platform 30, and the two anchoring stems 40 and 42 cooperatively define a single anchoring post 56 for the tibial component 14. The two antirotation fins 46 and 48 are positioned to extend outwardly in opposite directions from this post 56.

The two tibial tray members 18 and 20 are implanted with respect to the resected tibia 16 as an assembled unit. In this regard, implantation is best performed using a single driving tool (not shown) adapted to engage both tray members during driving placement of the anchoring post 56 and the associated fins 46 and 48 into the exposed cancellous bone 38. When the tray members 18 and 20 are properly implanted and seated as an assembled unit, a pair of meniscal bearing components 58 and 60 are respectively mounted on the platform members 32 and 34, for example, by snap-fit engagement with short locator pins 62 and 64 projecting upwardly from the platform members. These bearing components 58 and 60 include oval shaped recessed seats 66 and 68 (FIG. 3) on the upper surfaces thereof for supporting the femoral condyles 22 and 24 during postoperative use of the reconstructed knee. The bearing components are typically formed from a high density bearing plastic, such as polyethylene, and have individually selected heights to obtain a controlled or minimum laxity in the knee joint, with selected varus or valgus.

In postoperative use, the two tibial tray members 18 and 20 provide stable support for the femoral condyles 22 and 24. Importantly, through the full range of knee joint loading and motion, the slide key 52 and the key track 54 interlock the two tray members against relative motion in the anterior-posterior and the medial-lateral directions. This interlock functions to stabilize the entire tibial component 14 against undesired rocking or tipping or teetering which might otherwise cause the prosthesis to work loose and fail. However, in the event of subsidence in the longitudinal direction of compression loading, for any reason, the slide key arrangement permits relative movement between the tray members 18 and 20 (FIG. 6) to correspondingly permit both tray members to remain in intimate fixation with the patient bone. To the extent subsidence permits sufficient tray member shifting in the longitudinal direction to create unacceptable varus or valgus, a simple subsequent surgery may replace one or both of the meniscal bearing components 58 and 60 with appropriately resized components for improved knee alignment. Importantly, however, failure of the tibial component 14 and its interlock with patient bone are avoided.

A wide variety of modifications and improvements to the improved tibial component described herein will be apparent to those skilled in the art. For example, many different prosthesis slide interlock arrangements may be provided. Moreover, although traditional metal implant materials such as titanium or titanium alloys, cobalt, chrome, and the like are contemplated, alternative materials having functional elasticity features may be used particularly in the region of the key arrangement for interlocking the tibial tray members. As one illustrative example, the medial tray member could be constructed from a material having a different modulus of elasticity relative to the lateral member to permit better support of the typically more heavily loaded medial condyle with less relative subsidence. As another alternative, the tibial tray members may additionally include bone screws for improved stability during an initial postoperative phase as bone ingrowth proceeds. Accordingly, no limitation on the invention is intended by way of the description herein or the accompanying drawings, except as set forth in the appended claims.

What is claimed is:

1. In a tibial component for a knee prosthesis, the improvement comprising:
   a tibial platform defining by medial and lateral tibial tray members;
   means for interconnecting said medial and lateral tibial tray members to permit shifting therebetween constrained substantially to a single axis; and
   a pair of meniscal bearing components mounted respectively on said medial and lateral tibial tray members.

2. A tibial component for fixation to the upper end of a patient's tibia, for use in a knee prosthesis, said tibial component comprising:
   a pair of tibial tray members;
   means for interconnecting said tibial tray members, said tibial tray members when interconnected defining a tibial platform, at least one anchoring post projecting downwardly from said tibial platform, and at least one antirotation fin projecting generally radially outwardly from said anchoring post;
   said interconnecting means permitting shifting between said tibial tray members substantially along a single axis of the prosthesis when said tibial component is fixated to the patient's tibia; and
   a pair of meniscal bearing components mounted respectively on said pair of tibial tray members.

3. The tibial component of claim 2 wherein said meniscal bearing components are removably mounted on said tibial tray members.

4. The tibial component of claim 2 wherein each of said tibial tray members includes at least one region thereon carrying a selected porous bone ingrowth material coating.

5. The tibial component of claim 1 wherein said interconnecting means includes means for preventing shifting between said tibial tray members in the anterior-posterior direction and the medial-lateral direction when said tibial component is fixated to the patient's tibia.

6. The tibial component of claim 5 wherein said interconnecting means comprises a slide key on one of said tibial tray members for sliding reception into a mating key track formed on the other of said tibial tray members.

7. The tibial component of claim 6 wherein said slide key and said key track have generally dovetail shaped configurations.

8. The tibial component of claim 1 wherein each of said tibial tray members comprises a platform member, an anchoring stem projecting downwardly from said platform member, and an antirotation fin projecting generally laterally outwardly from said anchoring stem, and further wherein said platform members of said tibial tray members cooperatively define said tibial platform and said anchoring stems cooperatively define said anchoring post when said tray members are interconnected.

9. A tibial component for fixation to the upper end of a patient's tibia, for use in a knee prosthesis, said tibial component comprising:
   medial and lateral tibial tray members each including a platform member, and an anchoring stem projecting downwardly from at least one of said platform members;
   means for slidably interconnecting said tibial tray members in a medial-lateral arrangement with said platform members cooperating to define a tibial platform, said interconnecting means permitting positional shifting between said tibial tray member substantially along a single axis corresponding generally with a longitudinal axis of the prosthesis when said tibial component is fixated to the patient's tibia; and
   a pair of meniscal bearing components mounted respective on said pair of tibial tray members.

10. The tibial component of claim 9 wherein said meniscal bearing components are removably mounted on said tibial tray members.

11. The tibial component of claim 9 wherein each of said tibial tray members includes at least one region thereon carrying a selected porous bone ingrowth material coating.

12. The tibial component of claim 9 wherein said interconnecting means includes means for preventing shifting between said tibial tray members in the anterior-posterior direction and the medial-lateral direction when said tibial component is fixated to the patient's tibia.

13. The tibial component of claim 9 wherein each of said tibial tray members includes an anchoring stem projecting downwardly from the platform member thereof, said anchoring stems cooperating to define an anchoring post when said tray members are interconnected.

14. A tibial component for fixation to the upper end of a patient's tibia, for use in a knee prosthesis, said tibial component comprising:
   medial and lateral tibial tray members, each of said medial and lateral tibial tray members including a platform member, an anchoring stem projecting downwardly from said platform member, and an antirotation fin;
   slide means for interconnecting said tibial tray members for shifting constrained to a single axis corresponding generally with a longitudinal axis of the prosthesis when said tibial component is fixated to the patient's tibia;
   said platform members of said medial and lateral tibial tray members cooperatively defining a tibial platform and said anchoring stems of said medial and lateral tray members cooperatively defining an anchoring post when said tray members are interconnected, said antirotation fins of said medial and lateral tibia tray members projecting outwardly from said post generally in opposite directions; and
   a pair of meniscal bearing components mounted respectively on said pair of tibial tray members.

* * * * *